(12) United States Patent
Levanon

(10) Patent No.: US 9,892,155 B2
(45) Date of Patent: Feb. 13, 2018

(54) SYSTEM AND METHOD FOR SELECTION OF DATA ACCORDING TO MEASUREMENT OF PHYSIOLOGICAL PARAMETERS

(71) Applicant: BEYOND VERBAL COMMUNICATION LTD, Tel Aviv (IL)

(72) Inventor: Yoram Levanon, Ramat Hasharon (IL)

(73) Assignee: BEYOND VERBAL COMMUNICATION LTD, Tel Aviv (IL)

(*) Notice: Subject to any disclaimer, the term of this patent is extended or adjusted under 35 U.S.C. 154(b) by 339 days.

(21) Appl. No.: 14/425,958

(22) PCT Filed: Sep. 1, 2013

(86) PCT No.: PCT/IL2013/050738
§ 371 (c)(1),
(2) Date: Mar. 4, 2015

(87) PCT Pub. No.: WO2014/037937
PCT Pub. Date: Mar. 13, 2014

(65) Prior Publication Data
US 2015/0234886 A1  Aug. 20, 2015

Related U.S. Application Data

(60) Provisional application No. 61/697,316, filed on Sep. 6, 2012.

(51) Int. Cl.
*G06F 7/00* (2006.01)
*G06F 17/30* (2006.01)

(52) U.S. Cl.
CPC .. *G06F 17/30386* (2013.01); *G06F 17/30598* (2013.01)

(58) Field of Classification Search
CPC ......... G06F 17/30864; G06F 17/30598; G06F 17/30705; G06F 17/30867; G06F 17/3071
(Continued)

(56) References Cited

U.S. PATENT DOCUMENTS 8,078,470 B2   12/2011  Levanon et al.
8,140,391 B2   3/2012   Jacobi et al.
(Continued)

OTHER PUBLICATIONS

United States Patent and Trademark Office, "International Search Report in corresponding International Application No. PCT/IL2013/050738" dated Jan. 10, 2014.

*Primary Examiner* — Hosain Alam
*Assistant Examiner* — Nicholas Allen

(57) ABSTRACT

It is one object of the present invention to disclose a method for filtering targeted data comprising steps of: a. providing a plurality of M devices $D_i$; each of the $D_i$ is adapted to measure a physiological parameter; b. providing a data base of plurality of classified data; the classification is according to the physiological parameters; c. measuring a plurality of N physiological parameters of a mammalian subject using the devices; d. storing results of the measurement in a computer readable medium having instruction thereon; wherein the method, additionally comprising step of e. selecting via the instructions, at least some of the classified data according to the result of measurement of physiological parameters.

16 Claims, 3 Drawing Sheets

(58) Field of Classification Search
USPC .......................................................... 707/737
See application file for complete search history.

(56) References Cited

U.S. PATENT DOCUMENTS

| | | | | |
|---|---|---|---|---|
| 2002/0002464 | A1* | 1/2002 | Petrushin | G10L 17/26 704/275 |
| 2004/0030531 | A1* | 2/2004 | Miller | A61B 5/0002 702/182 |
| 2008/0046320 | A1* | 2/2008 | Farkas | G06Q 30/00 705/14.73 |
| 2008/0065468 | A1* | 3/2008 | Berg | G06Q 30/02 705/7.32 |
| 2008/0221401 | A1 | 9/2008 | Derchak et al. | |
| 2008/0270123 | A1* | 10/2008 | Levanon | G10L 17/26 704/200.1 |
| 2009/0112695 | A1 | 4/2009 | Jung et al. | |
| 2009/0125462 | A1* | 5/2009 | Krishnaswamy | G06Q 30/02 706/12 |
| 2009/0222305 | A1* | 9/2009 | Berg, Jr. | G06Q 30/00 705/7.29 |
| 2010/0134257 | A1* | 6/2010 | Puleston | G06K 7/0008 340/10.4 |
| 2010/0153389 | A1* | 6/2010 | Angell | G06Q 10/10 707/736 |
| 2010/0185064 | A1* | 7/2010 | Bandic | A61B 5/0059 600/306 |
| 2011/0035287 | A1* | 2/2011 | Fox | G06Q 30/02 705/14.69 |
| 2011/0093249 | A1* | 4/2011 | Holmes | G06F 19/3493 703/6 |
| 2011/0270813 | A1* | 11/2011 | Cok | G06Q 30/00 707/705 |
| 2011/0295843 | A1* | 12/2011 | Ingrassia, Jr. | G06F 17/30053 707/723 |
| 2012/0035428 | A1* | 2/2012 | Roberts | A61B 5/165 600/300 |
| 2012/0036005 | A1* | 2/2012 | Pradeep | G06Q 30/02 705/14.41 |
| 2012/0039809 | A1* | 2/2012 | Levinson | A61B 10/0045 424/9.1 |
| 2012/0071731 | A1* | 3/2012 | Gottesman | A61B 5/486 600/301 |
| 2012/0083668 | A1 | 4/2012 | Pradeep et al. | |
| 2012/0084139 | A1 | 4/2012 | Pradeep et al. | |
| 2012/0110082 | A1* | 5/2012 | Brown | G06F 17/30731 709/204 |
| 2012/0110458 | A1* | 5/2012 | Brown | G06F 17/30575 715/733 |
| 2012/0164613 | A1* | 6/2012 | Jung | G06Q 30/02 434/236 |
| 2015/0234886 | A1* | 8/2015 | Levanon | G06F 17/30598 707/737 |
| 2016/0015307 | A1* | 1/2016 | Kothuri | A61B 5/167 702/19 |

* cited by examiner

SYSTEM AND METHOD FOR SELECTION OF DATA ACCORDING TO MEASUREMENT OF PHYSIOLOGICAL PARAMETERS

FIELD OF THE INVENTION

The current invention relates to the field of producing targeted data and to the measurement of physiological parameters. More specifically, it combines the two in order to optimize the selection of the targeted data.

BACKGROUND

The analysis of user's behavior in order to personalize targeted data is a growing field. Targeted data is especially important for advertisement, usually, shopping data is analyzed in order to produce special offers which are targeted to specific shopping pattern.

United states patent U.S. Pat. No. 8,140,391 claims computer implemented method for selecting items for a user using analysis of previous user behavior. However, this patent does not uses any physiological parameters for the selection process, it only derives its recommendation from past behaviors.

United states patent U.S. Pat. No. 8,078,470 claims a method and means for indicating emotional response using physiological parameters. However, this patent does not make any use of the identified emotional state of the subject.

There is therefore a long unmet need for a method and mean that will be able to use physiological parameters in order to improve the selection of targeted data.

SUMMARY OF THE INVENTION

It is one object of the present invention to disclose a method for filtering targeted data comprising steps of:
 a. providing a plurality of M devices $D_i$; each of the $D_i$ is adapted to measure a physiological parameter;
 b. providing a data base of plurality of classified data; the classification is according to the physiological parameters;
 c. measuring a plurality of N physiological parameters of a mammalian subject using the devices;
 d. storing results of the measurement in a computer readable medium having instruction thereon;
 wherein the method, additionally comprising step of
 e. selecting via the instructions, at least some of the classified data according to the result of measurement of physiological parameters.

It is another object of the current invention to disclose the method as defined above, additionally comprising step prior to step (e) consisting of deriving from the measurement emotional state of the mammalian subject via the instructions.

It is another object of the current invention to disclose the method as defined above, additionally comprising step of selecting the classified data according to the emotional state.

It is another object of the current invention to disclose the method as defined above, wherein the classification is for categories selected from a group consisting of: range of measurement result, absolute value of measurement result, combination of a few measurements and a combination thereof.

It is another object of the current invention to disclose the method as defined above, wherein the classified data is selected from a group consisting of: coupons, marketing data, informational data, social data, matching data between individuals in a social network, and any combination thereof.

It is another object of the current invention to disclose the method as defined above, wherein physiological parameter is selected from a group consisting of: skin conductivity, rate of heart beat, blood pressure, brain activity, smell, voice intonation, facial expression, eye movement, voice tone, body language.

It is another object of the current invention to disclose the method as defined above, wherein device is selected from a group consisting of: voice recorder, camera, a module adapted to measure eye movement; a module adapted to measure skin conductivity, a module adapted to measure rate of heart beat, a module adapted to measure blood pressure, a module adapted to measure brain activity, a module adapted to measure smell, a module adapted to measure voice intonation, a module adapted to measure facial expression, a module adapted to measure voice tone, a module adapted to measure body language.

It is another object of the current invention to disclose the method as defined above, wherein mammalian are selected from a group consisting of: primates, dogs, cat and any other member of the mammalian group.

It is another object of the current invention to disclose the method as defined above, additionally comprising step of delivering the selected data to a computerized module.

It is another object of the current invention to disclose the method as defined above, wherein the computerized device is selected from a group consisting of: mobile device, personal computer, tablet, cash register, laptop, electronic screen, and any combination thereof.

It is another object of the current invention to disclose the method as defined above, additionally comprising step of accumulating data of at least one specific user.

It is another object of the current invention to disclose the method as defined above, wherein said step (e) of selecting is according to said accumulated data.

It is one object of the present invention to disclose a system for filtration of targeted data comprising:
 a. a plurality of M devices $D_i$; each of the $D_i$ is adapted to measure a physiological parameter of mammalian subject;
 b. a first data base of plurality of classified data; the classification is according to the physiological parameters;
 c. a computer readable medium CRM having instruction thereon for storing results of the measurements; the CRM is in communication with the M devices, the data base;
 wherein the instructions are additionally for selecting at least some of the classified data according to the result of measurement of physiological parameters.

It is another object of the current invention to disclose the system as defined above, wherein the instructions are additionally deriving from the measurement emotional state of the mammalian subject prior to the selection.

It is another object of the current invention to disclose the system as defined above, wherein the classified data is selected according to the emotional state.

It is another object of the current invention to disclose the system as defined above, wherein the classification is for categories selected from a group consisting of: range of measurement result, absolute value of measurement result, combination of a few measurements and a combination thereof.

It is another object of the current invention to disclose the system as defined above, wherein the classified data is selected from a group consisting of: coupons, marketing data, informational data, social data, matching data between individuals in a social network, and any combination thereof.

It is another object of the current invention to disclose the system as defined above, wherein physiological parameter is selected from a group consisting of: skin conductivity, rate of heart beat, blood pressure, brain activity, smell, voice intonation, facial expression, eye movement, voice tone, body language.

It is another object of the current invention to disclose the system as defined above, wherein device is selected from a group consisting of: voice recorder, camera, a module adapted to measure eye movement; a module adapted to measure skin conductivity, a module adapted to measure rate of heart beat, a module adapted to measure blood pressure, a module adapted to measure brain activity, a module adapted to measure smell, a module adapted to measure voice intonation, a module adapted to measure facial expression, a module adapted to measure voice tone, a module adapted to measure body language.

It is another object of the current invention to disclose the system as defined above, wherein mammalian are selected from a group consisting of: primates, dogs, cat and any other member of the mammalian group.

It is another object of the current invention to disclose the system as defined above, wherein the selected classified data is delivered to a computerized module.

It is another object of the current invention to disclose the system as defined above, wherein the computerized device is selected from a group consisting of: mobile device, personal computer, tablet, cash register, laptop, electronic screen, and any combination thereof.

It is another object of the current invention to disclose the system as defined above, wherein said CRM is adapted to accumulate data of at least one specific user.

It is another object of the current invention to disclose the system as defined above, wherein said step (e) of selecting is according to said accumulated data.

BRIEF DESCRIPTION OF THE DRAWINGS

In order to understand the invention and to see how it may be implemented in practice, a few preferred embodiments will now be described, by way of non-limiting example only, with reference to be accompanying drawings, in which.

DETAILED DESCRIPTION OF THE INVENTION

The following description is provided so as to enable any person skilled in the art to make use of the invention and sets forth examples contemplated by the inventor of carrying out this invention. Various modifications, however, will remain apparent to those skilled in the art, since the generic principles of the present invention have been defined specifically. Also, it is to be understood that the phraseology and terminology employed herein is for the purpose of description and should not be regarded as limiting.

It is one object of the present invention to disclose a method for filtering targeted data comprising steps of:
a. providing a plurality of M devices $D_i$; each of the $D_i$ is adapted to measure a physiological parameter;
b. providing a data base of plurality of classified data; the classification is according to the physiological parameters;
c. measuring a plurality of N physiological parameters of a mammalian subject using the devices;
d. storing results of the measurement in a computer readable medium having instruction thereon;
wherein the method, additionally comprising step of
e. selecting via the instructions, at least some of the classified data according to the result of measurement of physiological parameters.

It is another object of the present invention to disclose a system for filtration of targeted data comprising:
a. a plurality of M devices $D_i$; each of the $D_i$ is adapted to measure a physiological parameter of mammalian subject;
b. a first data base of plurality of classified data; the classification is according to the physiological parameters;
c. a computer readable medium CRM having instruction thereon for storing results of the measurements; the CRM is in communication with the M devices, the data base;
wherein the instructions are additionally for selecting at least some of the classified data according to the result of measurement of physiological parameters.

The term "emotional state", refers hereinafter to any emotion of: affection, anger, angst, anguish, annoyance, anxiety, apathy, arousal, awe, boldness, boredom, contempt, contentment, curiosity, depression, desire, despair, disappointment, disgust, distrust, dread, ecstasy, embarrassment, envy, euphoria, excitement, fear, fearlessness, frustration, gratitude, grief, guilt, happiness, hatred, hope, horror, hostility, hurt, hysteria, indifference, interest, jealousy, joy, loathing, loneliness, love, lust, misery, panic, passion, pity, pleasure, pride, rage, regret, remorse, sadness, satisfaction, shame, shock, shyness, sorrow, suffering, surprise, terror, trust, wonder, worry, zeal, zest, lack of interest, self-control, interpersonal communication, pragmatism, survival, conservatism, creativeness, inspiration, leadership, authority, preaching, admiring, envying, aggressiveness, hypocrisy, possessiveness, and any combination thereof.

Figure 1:
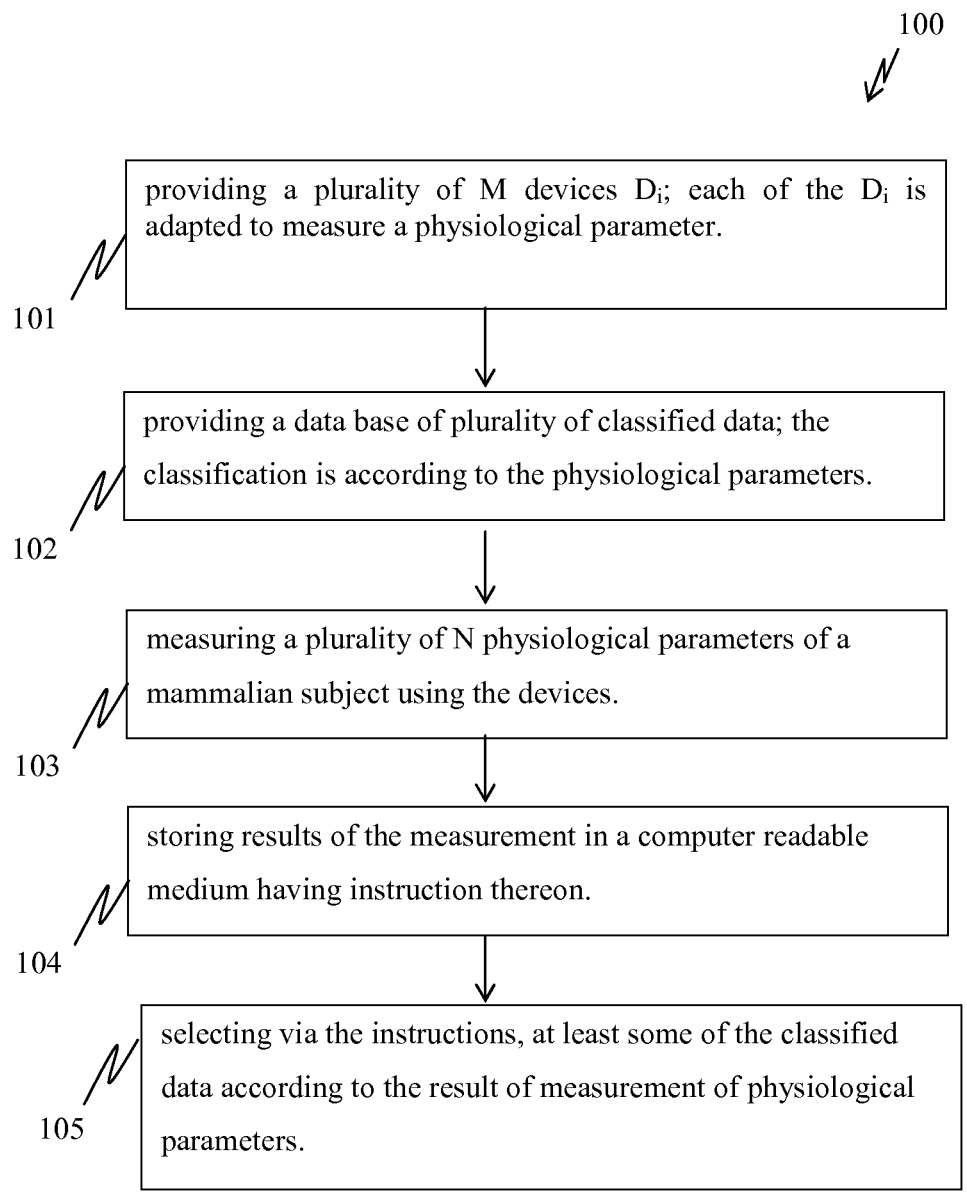
FIG. 1 describes a flow chart of a method for filtering targeted data.

Reference is made to FIG. 1, illustrating in a non-limiting manner a method 100 for filtering targeted data comprising:
a. step 101 of providing a plurality of M devices $D_i$; each of the $D_i$ is adapted to measure a physiological parameter;
b. step 102 providing a data base of plurality of classified data; the classification is according to the physiological parameters;
c. step 103 measuring a plurality of N physiological parameters of a mammalian subject using the devices;
d. step 104 storing results of the measurement in a computer readable medium having instruction thereon;
wherein the method, additionally comprising step of
e. step 105 selecting via the instructions, at least some of the classified data according to the result of measurement of physiological parameters.

Figure 2:
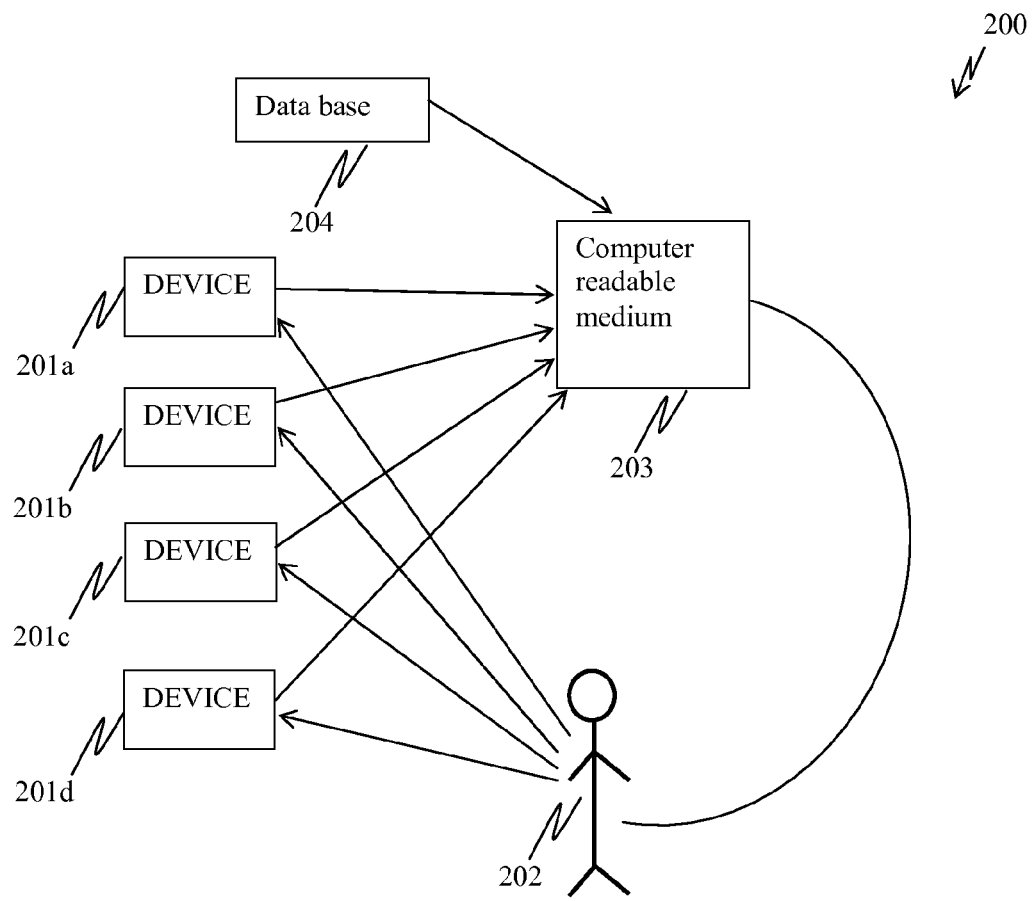
FIG. 2 reveals a system for selecting targeted data.

Reference is now made to FIG. 2 describing in a non-limiting manner a system 200 for filtration of targeted data comprising:

a. a plurality of M devices $D_i 201(a-d)$; each of the $D_i 201(a-d)$ is adapted to measure a physiological parameter of mammalian subject 202;
b. a data base 204 of plurality of classified data; the classification is according to the physiological parameters;
c. a computer readable medium CRM 203 having instruction thereon for storing results of the measurements; the CRM 203 is in communication with the M devices 201(a-d), the data base 204;

wherein the instructions are additionally for selecting at least some of the classified data according to the result of measurement of physiological parameters.

Figure 3:
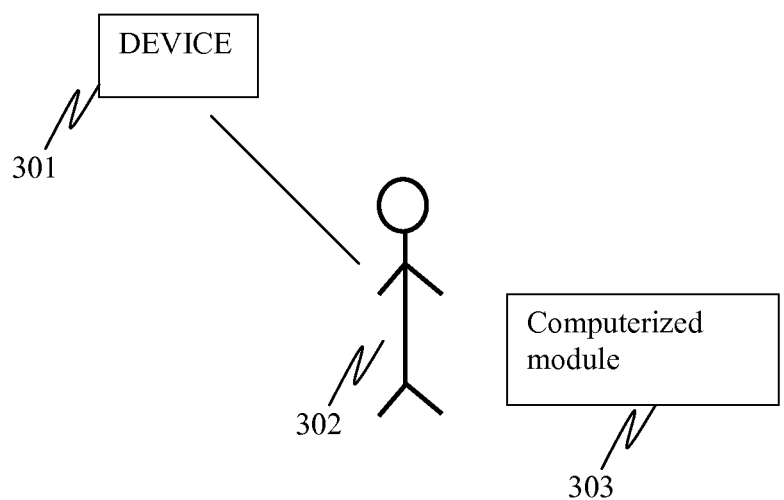
FIG. 3 shows a system for measuring a human physiological parameters and sending him information following the measurement.

Reference is now made to FIG. 3, illustrating in a non-limiting manner, a device 300 performing a measurement on a human 302. According to the measurement results information is sent to the human 302 electronic device 303.

In some embodiments of the current invention, the measurement of the physiological parameters is followed by a step of analyzing the data and deriving the emotional status of the subject which was measured. This emotional status is then used in order to select the targeted data. For example, it may produce matching to potential partners according to character; it may give marketing information relying on the mental status s of the customer etc.

In some embodiment of the current invention, the data in the data base may be classified to match emotional state of the subject being tested; other parameters may affect the selection as well, such as marketing information of health recommendation. There is therefore a possibility for the system to perform the selection either according to the emotional state of the subject or directly from the physiological parameters being tested. Reference U.S. Pat. No. 8,078,470 incorporated entirely herein demonstrates identifying subject health status according to voice analysis; the current invention will produce a second stage in which data is produced according to the results of this analysis.

In some embodiment of the current invention, the classification of the data is for categories selected from a group consisting of: range of measurement result, absolute value of measurement result, combination of a few measurements and a combination thereof. That is, the result of the measurements may lay on a discrete or a continuous range for the next analysis procedure.

In some embodiment of the current invention, the classified data is selected from a group consisting of: coupons, marketing data, informational data, social data, matching data between individuals in a social network, and any combination thereof.

In some embodiment of the current invention, physiological parameter is selected from a group consisting of: skin conductivity, rate of heart beat, blood pressure, brain activity, smell, voice intonation, facial expression, eye movement, voice tone, body language.

In some embodiment of the current invention, device is selected from a group consisting of: voice recorder, camera, a module adapted to measure eye movement; a module adapted to measure skin conductivity, a module adapted to measure rate of heart beat, a module adapted to measure blood pressure, a module adapted to measure brain activity, a module adapted to measure smell, a module adapted to measure voice intonation, a module adapted to measure facial expression, a module adapted to measure voice tone, a module adapted to measure body language.

In some embodiments of the current invention, the mammalian are selected from a group consisting of: primates, dogs, cat and any other member of the mammalian group.

In some embodiments of the current invention, the targeted data after its selection is sent to the subject via an electronic device, it may also be sent for example to a doctor or a database or may be to a Point of sale.

In some embodiments of the current invention the computerized device may be selected from a group consisting for example of: mobile device, personal computer, tablet, cash register, laptop, electronic screen, and any combination thereof.

In some embodiments of the current invention, measurements or emotions of a user (may also be a plurality of users) are accumulated over time. The accumulated data is then used to additionally optimize the selection of the targeted data.

Example 1

In one example of the current invention certain targeted information will be associated in a database with a specific emotional status. That is, once a detection by a designated module (measuring a variety of physiological parameters) of adventurous emotional status is found, a hiking show commercial will appear on a user's mobile device. The mobile device may be used in that case as the measurement module, as it can measure the heart rate of a user and the sweating in its palms.

Example 2

A telephone conversation is taking place, and the tone of the voice is analyzed, according to the results of the tone analysis, an e-mail with a commercial may be sent to the user's laptop.

Example 3

A television device detected a specific user watching the television, there is a camera in communication with the television, and the camera detects that the user is at ease and relaxing. The television in this case may be adapted to automatically switch channels to a classical music channel.

Example 4

A costumer is walking in a store; the store has modules spread around for detecting smell. The modules detect smells associated with a certain illness, once the costumer is arriving to the cash register an offer is produced for him for medication.

Example 5

A user is playing an augmented reality game, in which the user is characterized by a figure in the augmented world, the game is equipped with sensors which can detect the physiological parameters of the user and use them within the augmented reality.

Example 6

A dating application is installed on a mobile device; the application uses the camera of the mobile device and other installed modules to detect: eye movement and sweating. According to the detected parameters, the application decides the temper of the user and according to the detected temper; it chooses potential dating options for the user.

Example 7

A dog and its owner is entering a pet store, in the pet store there is a module to detect smell of leeches. Once the dog is detected by the module with leeches a spray will automatically be spraying the dog as he walks out of the store.

Example 8

A person is using a social network, he has a module for measuring his mental state, using this module and the network, the data is being published. Following the publication, the person will receive advice regarding his mental state from his network.

Example 9

A patient is being measured by a device to detect its physical/emotional state while he is at home, the device performs the measurement on a daily basis, and produces treatment recommendations according to the results of the measurement. Once a week, the device is adapted to analyze the entire accumulated medical history of the patient (according to the measurements), and produce a health status report of the patient progress.

Example 10

A user is using a mobile device which is adapted to measure heart beat rate and sweating, these physical measurements are then translated to an emotional state. An application on the mobile device analyses the emotional state data over time, and produces marketing information the the user according to the most frequent emotion detected during a predetermined time length.

It will be appreciated by persons skilled in the art that embodiment of the invention are not limited by what has been particularly shown and described hereinabove. Rather the scope of at least one embodiment of the invention is defined by the claims below.

The invention claimed is:

1. A method for filtering targeted data comprising steps of:
  a. providing a plurality of M devices $D_i$; each of said $D_i$ is adapted to measure a physiological parameter; at least one of said physiological parameters being a voice-based physiological parameter selected from voice intonation and voice tone and at least one of said physiological parameters being a non-voice based physiological parameter selected from a group consisting of skin conductivity, rate of heart beat, blood pressure, brain activity, smell, facial expression, eye movement, and body language;
  b. providing a data base of plurality of classified data; said classification is according to said physiological parameters; wherein said classified data is selected from a group consisting of: coupons, marketing data, informational data, social data, matching data between individuals in a social network, and any combination thereof;
  c. measuring said at least one non-voice based physiological parameters of a mammalian subject using said devices;
  d. measuring said voice intonation or voice tone and determining at least one voice-based emotional attitude, as follows:
    i. obtaining a database comprising reference tones and voice-based reference emotional attitudes corresponding to each of said reference tones;
    ii. pronouncing at least one word by a speaker for the duration of a sample period;
    iii. recording said at least one word so as to obtain a signal representing sound volume as a function of frequency for said sample period;
    iv. processing said signal so as to obtain voice characteristics of said speaker, wherein said processing includes determining a Function A, said Function A being defined as the average or maximum sound volume as a function of sound frequency, from within a range of frequencies measured in said sampled period, and wherein said processing further includes determining a Function B, said Function B defined as the averaging, or maximizing of said function A over said range of frequencies and dyadic multiples thereof;
    v. comparing said voice characteristics to said reference tones so as to indicate at least one of said voice-based reference emotional attitudes;
  e. storing results of said measurements and said voice-based emotional attitude in a computer readable medium having instruction thereon;
  wherein said method, additionally comprising steps of
  f. deriving, from said at least one voice-based emotional attitude and said at least one non-voice based physiological parameter, an emotional state of said mammalian subject via said instructions; and
  g. selecting via said instructions, at least some of said classified data according to said emotional state.

2. The method according to claim 1, wherein said classification is for categories selected from a group consisting of: range of measurement result, absolute value of measurement result, combination of a few measurements and any combination thereof.

3. The method according to claim 1, wherein device is selected from a group consisting of: voice recorder, camera, a module adapted to measure eye movement; a module adapted to measure skin conductivity, a module adapted to measure rate of heart beat, a module adapted to measure blood pressure, a module adapted to measure brain activity, a module adapted to measure smell, a module adapted to measure voice intonation, a module adapted to measure facial expression, a module adapted to measure voice tone, a module adapted to measure body language.

4. The method according to claim 1, wherein mammalian are selected from a group consisting of: primates, dogs, cat and any other member of the mammalian group.

5. The method according to claim 1, additionally comprising step of delivering said selected data to a computerized module.

6. The method according to claim 5, wherein said computerized device is selected from a group consisting of: mobile device, personal computer, tablet, cash register, laptop, electronic screen, and any combination thereof.

7. The method according to claim 1, additionally comprising step of accumulating data of at least one specific user.

8. The method according to claim 7, wherein said step (e) of selecting is according to said accumulated data.

9. A system for filtration of targeted data comprising:
  a. a plurality of M devices $D_i$; each of said $D_i$ is adapted to measure a physiological parameter of mammalian subject; at least one of said physiological parameters being a voice-based physiological parameter selected from voice intonation and voice tone and at least one of said physiological parameters being a non-voice based physiological parameter selected from a group consisting of skin conductivity, rate of heart beat, blood pressure, brain activity, smell, facial expression, eye movement, and body language;

b. a data base of plurality of classified data; said classification is according to said physiological parameters; wherein said classified data is selected from a group consisting of: coupons, marketing data, informational data, social data, matching data between individuals in a social network, and any combination thereof;

c. a computer readable medium CRM having instruction thereon for storing results of said measurements; said CRM is in communication with said M devices, said data base;

d. a sub-system for indicating at least one voice-based emotional attitude of a speaker using voice tone analysis, said sub-system comprising:

i. a sound recorder adapted to record a word or set of words that is repeatedly pronounced by a speaker for the duration of a sample period, and to produce a signal representing sound volume as a function of frequency for said sample period;

ii. processing means coupled to said recorder, for processing said signal so as to obtain voice characteristics relating to the tone of said speaker, wherein said voice characteristics includes a Function A defined as the average or maximum sound volume as a function of sound frequency from within a range of frequencies measured in said sampled period and a Function B defined as the averaging, or maximizing of said function A over said range of frequencies and dyadic multiples thereof; and iii. a database comprising a plurality of reference tones and emotional attitudes corresponding to each of said reference tones for allowing indicating of at least one voice-based emotional attitude of said speaker through comparison of said voice characteristics to said reference tones;

wherein said instructions are additionally for e. deriving, from said at least one voice-based emotional attitude and said at least one non-voice based physiological parameter, an emotional state of said mammalian subject; and f. selecting at least some of said classified data according to said emotional state, selecting at least some of said classified data according to said result of measurement of physiological parameters.

10. The system according to claim 9, wherein said classification is for categories selected from a group consisting of: range of measurement result, absolute value of measurement result, combination of a few measurements and a combination thereof.

11. The system according to claim 9, wherein device is selected from a group consisting of: voice recorder, camera, a module adapted to measure eye movement; a module adapted to measure skin conductivity, a module adapted to measure rate of heart beat, a module adapted to measure blood pressure, a module adapted to measure brain activity, a module adapted to measure smell, a module adapted to measure voice intonation, a module adapted to measure facial expression, a module adapted to measure voice tone, a module adapted to measure body language.

12. The system according to claim 9, wherein mammalian are selected from a group consisting of: primates, dogs, cat and any other member of the mammalian group.

13. The system according to claim 9, wherein said selected classified data is delivered to a computerized module.

14. The system according to claim 12, wherein said computerized device is selected from a group consisting of: mobile device, personal computer, tablet, cash register, laptop, electronic screen, and any combination thereof.

15. The system according to claim 9, wherein said CRM is adapted to accumulate data of at least one specific user.

16. The system according to claim 15, wherein said step (e) of selecting is according to said accumulated data.

\* \* \* \* \*